United States Patent [19]

Caldero Ges et al.

[11] Patent Number: 5,658,916
[45] Date of Patent: Aug. 19, 1997

[54] DRUG ACTIVE ON THE CENTRAL NERVOUS SYSTEM, A PROCESS FOR THE PREPARATION THEREOF AND PHARMACEUTICAL COMPOSITIONS CONTAINING IT

[75] Inventors: José Maria Caldero Ges, Barcelona; Joan Huguet Clotet, Sant Joan Despi; Francisco Marquillas Olóndriz, Barcelona; Pere Dalmases Barjoan, Sant Feliu De Llobregat; Anna Bosch Rovira, Barcelona; Joan Roca Acín, Barcelona; Juan Carlos Del Castillo Nieto, Barcelona, all of Spain

[73] Assignee: Vita-Invest, S.A., Barcelona, Spain

[21] Appl. No.: 532,672

[22] PCT Filed: Feb. 2, 1995

[86] PCT No.: PCT/ES95/00015

§ 371 Date: Oct. 12, 1995

§ 102(e) Date: Oct. 12, 1995

[87] PCT Pub. No.: WO95/23144

PCT Pub. Date: Aug. 31, 1995

[30] Foreign Application Priority Data

Feb. 24, 1994 [ES] Spain .................... 9400362

[51] Int. Cl.$^6$ .................... C07D 403/14; C07D 401/14; A61K 31/505
[52] U.S. Cl. .................... 514/258; 544/282; 546/272.1
[58] Field of Search .................... 544/282; 514/258

[56] References Cited

U.S. PATENT DOCUMENTS 5,158,952 10/1992 Janssen et al. .................... 514/258
5,482,943 1/1996 Kennis et al. .................... 514/258

FOREIGN PATENT DOCUMENTS 0037265 3/1981 European Pat. Off. .................... 471/4
0196132 3/1986 European Pat. Off. .................... 413/14
368388A 5/1990 European Pat. Off. .
453042A 10/1991 European Pat. Off. .
553419A 3/1986 Spain .................... 413/14

OTHER PUBLICATIONS

R.E. Lyle et al., *The Reduction of Nitrogen Heterocycles with Complex Metal Hydrides*, Chem. 6, pp. 45–93 (1966).
L. Davis et al., *Drug Design and Discovery*8, pp. 225–240 (1992).
F.J. Villani et al., *J. Org. Chem.* 17, p. 249 (1952).
H. Fujita et al., *Ann. Rep. Sankyo Res. Lab* 29, pp. 75–78 (1977).
J.E. Leysen et al., *Biochem. Pharmacol.*, 27: pp. 307–316 (1978).
A.L. Morrow et al., *Eur. J. Pharmacol*, 109: pp. 285–287 (1985).

*Primary Examiner*—Matthew V. Grumbling
*Attorney, Agent, or Firm*—Sughrue, Mion, Zinn, Macpeak & Seas

[57] ABSTRACT

The agent is the compound 3-{2-[4-(6-fluoro-benzo[d]isoxazol-3-yl)-3,6-dihydro-2H-pyridin-1-yl]-ethyl}-2-methyl-6,7,8,9-tetrahydropyrido [1,2-a]pyrimidin-4-one having the formula (I)

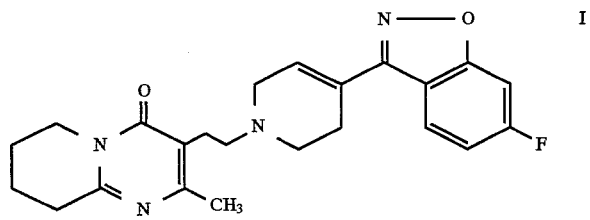

and pharmaceutically acceptable salts thereof; the process is based on the reduction of a selected pyridin salt by means of a metal borohydride; its preferred application is as an antipsychotic agent.

12 Claims, No Drawings

DRUG ACTIVE ON THE CENTRAL NERVOUS SYSTEM, A PROCESS FOR THE PREPARATION THEREOF AND PHARMACEUTICAL COMPOSITIONS CONTAINING IT

This is a 371 of PCT/ES95/00015 filed Feb. 2, 1995.

DESCRIPTION

The invention relates to a compound, 3-{2-[4-(6-fluoro-benzo[d]isoxazol-3-yl)-3,6-dihydro-2H-pyridin-1-yl]-ethyl}-2-methyl-6,7,8,9-tetrahydropyrido [1,2-a]pyrimidin-4-one, of

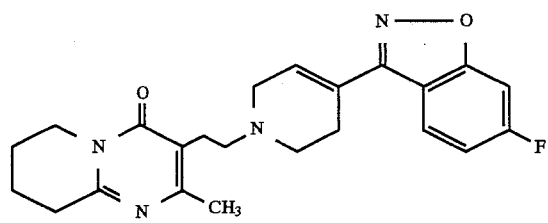

which is useful as a drug active on the central nervous system and to the pharmaceutically acceptable salts thereof.

BACKGROUND OF THE INVENTION

EP-A-O 196 132 describes 3-piperidinyl-1,2-benzoisoxazoles of formula (II) as having antipsychotic properties.

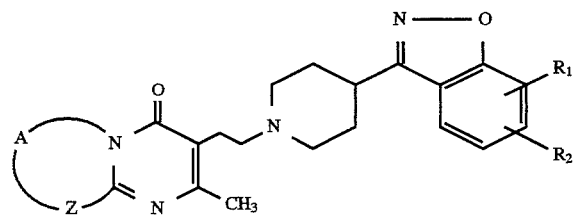

EP-A-O 037 265 describes 3-[(1-piperidinyl)-4H-pyrido-[1,2-a]pyrimidin-4-ones of formula (III)

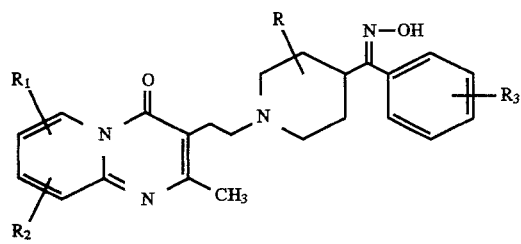

where R may be H, alkyl, OH, RO or $CH_2OH$ in positions 2, 3 or 4 of the piperidine ring, useful as cardiovascular agents and which act on the central nervous system.

The compound of formula (I) of the invention differs from the known compounds in the presence of a double bond between the 3 and 4 positions of the piperidine ring and in its pharmacological activity.

SUMMARY OF THE INVENTION

The compound 3-{2-[4-(6-fluoro-benzo[d]isoxazol-3-yl)-3,6-dihydro-2H-pyridin-1-yl]-ethyl}-2-methyl-6,7,8,9-tetra-hydroprido[1,2-a]pyrimidin-4-one of formula (I) of the invention has interesting pharmacological properties, particularly in the treatment of psychotic disorders and alterations related with the capturing and/or release of dopamine and/or serotonin.

The invention also provides a pharmaceutical composition comprising the compound of formula (I) or a pharmaceutically acceptable salt thereof, together with a pharmaceutically acceptable diluent. The composition is preferably for human use, in the form of tablets, capsules, injectables or suspension. Its use in the treatment of psychotic diseases is particularly outstanding.

The compound of formula (I) may be prepared by a process consisting of the reduction of the pyridinium salt of formula (IV)

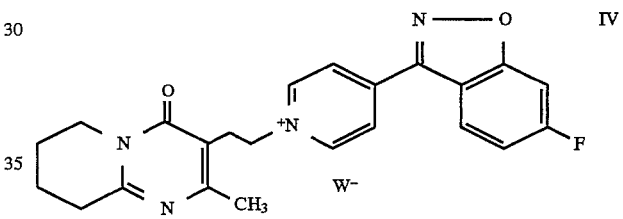

where $W^-$ is an organic or inorganic anion, such as a halide or a sulfonate.

The pyridinium salt of formula (IV) may be conveniently reduced with a metal borohydride, such as sodium borohydride, in an adequate protic solvent, such as water, alkanols or carboxylic acids. (R. E. Lyle and P. S. Anderson, Adv. Hetero-cycl. Chem. 6, 45–93 (1966)).

The intermediates and the starting compounds used in the process of the present invention are known products or may be easily prepared from known products.

The intermediates of formula (IV) may be easily prepared by N-alkylation of the pyridine of formula (V) with a reactant of formula (VI), where W is an appropriate leaving group such as, for example, a halide or a sulfonate.

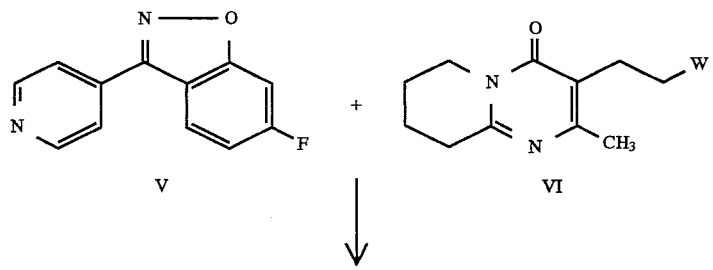

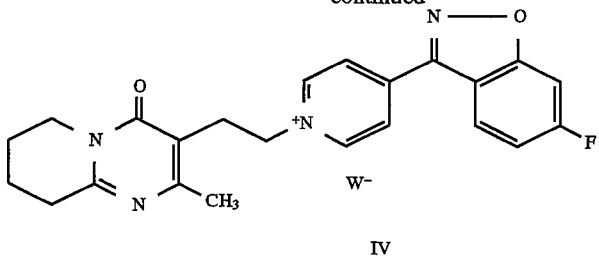

IV

The N-alkylation reaction is conducted in a solvent inert to the reaction, such as 4-methyl-2-pentanone, aceto-nitrile, N-methylpyrrolidone or N,N-dimethylformamide, optionally at a slightly raised temperature and adding potasium iodide as catalyst.

The pyridine of formula (V) may be obtained by cyclization of the oxime (VII) in an inert solvent, such as tetrahydrofurane, dioxane or N,N-dimethylformamide in the presence of an appropriate base, such as an alkaline carbonate or an alkaline hydride or alkoxide.

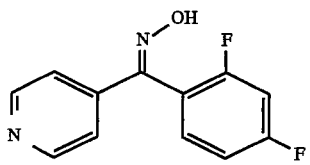

VII

Alternatively, the pyridine of formula (V) may also be prepared by cyclization of the acetylated derivative of formula (VIII) of the oxime of formula (IX) (L. Davis et Drug Design and Discovery, 8, 225–240 (1992)).

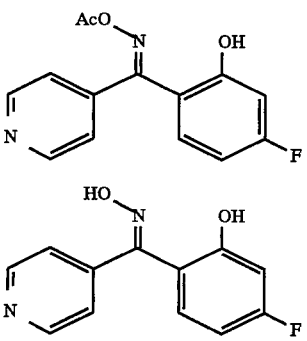

VIII

IX

The ketone of formula (X) precursor of (VII) may be prepared by Friedel-Crafts acylation of 1,3-difluorobenzene with isonicotinoyl chloride (F. J. Villani et al., J. Org. Chem. 17, 249 (1952)).

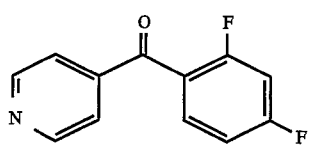

X

Likewise, the ketone of formula (XI) precursor of the oxime of formula (IX) may be prepared by Fries reaction, from 3-fluorophenol and isonicotinoyl chloride.

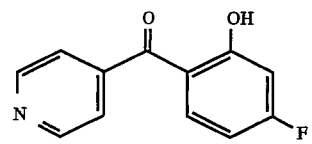

XI

The compounds of formula (VI) have been described (H. Fujita et al., Ann. Rep. Sankyo Res. Lab. 29, 75–98 (1977)).

The preferred pharmaceutically acceptable salts are the acid addition salts. The pharmaceutically acceptable addition salts of the compounds of formula (I) are those formed from acids forming non toxic addition salts, containing pharmaceutically acceptable anions. The salts may be derived from inorganic acids, such as hydrochloric, hydrobromic, sulfuric or nitric acid or organic acids, such as lactic, succinic, oxalic, maleic, etc. acids.

The salts may be prepared by conventional processes such as, fop example, by mixing solutions containing equimolecular amounts of the free base and the desired acid. The salt formed is recovered by filtration, if it is insoluble, or by evaporation of the solvent.

The compound of formula (I) and its pharmaceutically acceptable salts are very active as antipsychotic drugs.

PHARMACOLOGICAL RESULTS

Studies on binding to $D_2$ receptors.

These were carried out as described by Leysen et al (1978), with certain modifications. Striate tissue of rat brain was prepared, with homogenization in 20 volumes of Tris-HCl buffer in ice (50 mM, pH=7.7, 4° C.), The homogenate was centrifuged (40,000 g, 10 min) and the pellet was suspended in 10 volumes of cold buffer and recentrifuged. The final pellet was suspended in 10 volumes of 50 mM Tris-HCl buffer, with 120 mM of NaCl and 5 mM of HCl (pH=7.7). The displacement studies were carried out with 25 µl of $^3$H-spiroperidol (0.2 nM, NEN), 25 µl of cold displacer and 200 µl of tissue. The incubation (37° C., 15 min) was terminated by rapid filtering through Whatman GF/C filters. The unmarked reference product was haloperidol.

Studies on binding to $5HT_2$ receptors.

These were carried out as described by Leysen et al (1978), with certain modifications. Front cortex of rat brain was prepared, with homogenization in 20 volumes of Tris-HCl buffer in ice (50 mM, pH=7.4, 4° C.). The homogenate was centrifuged (40,000 g, 10 min) and the pellet was suspended in 10 volumes of cold buffer and recentrifuged. The final pellet was suspended in 400 ml of 50 mM Tris-HCl buffer. The displacement studies were carried out with 25 µl of $^3$H-Ketan-serine (0.5 nM, NEN), 25 µl of cold displacer and 500 µl of tissue. The incubation (37° C., 15 min) was terminated by rapid filtering through Whatman GF/C filters. The unmarked reference product was cyproheptadine.

Binding to at adrenergen receptors

These were carried out as described by Morrow et al. (1985), with certain modifications. $^3$H-prazosin bound with great affinity to $\alpha_1$-adrenergic receptors of rat brain cortex. Rat brain cortical tissue was obtained, with homogenization in 20 volumes of Tris-HCl buffer in ice (50 mM, pH=7.7, 4° C.). The homogenate was centrifuged (25,000 rpm/12 min at 4° C.) and the pellet was rehomogenized, being finally resuspended in 50 mM Tris-HCl buffer, pH=7.7 (dilution 1:200). For the assay, 0.9 ml of the homogenate were incubated with 50 μl of $^3$H-prazosin (0.5 nM) and 50 μl of the corresponding cold displacer at different concentrations. The incubation (37° C., 15 min) was terminated by rapid filtering through Whatman GF/C filters, followed by washing twice with ml of Tris-HCl buffer, 50 mM. The unmarked reference product is prazosin.

Leysen, J. E.; Goumeren, W. and Laduron, P. M. (1978). Biochem. Pharmacol., 27: 307–316.

Morrow et al. (1985). Eur. J. Pharmacol., 109: 285–287.

Displacement (Ki, nM) of the binding of $^3$H-spiroperidol to $D_2$ receptors (striate rat tissue), of $^3$H-ketanserine to 5-HT$_2$ receptors and of $^3$H-prazosin to $\alpha_1$-adrenergic receptors (rat cortex).

| COMPOUND | RECEPTORS | | |
|---|---|---|---|
| | $D_2$ | 5HT$_2$ | $\alpha_1$ |
| Haloperidol | 1.6 | 124 | 57.7 |
| Cyproheptadine | — | 2.5 | — |
| Prazosin | — | — | 0.3 |
| Ritanserine | 47.7 | 2.6 | 29.6 |
| Risperidone | 8.5 | 2.1 | 7.1 |
| Compound I | 22.0 | 1.7 | 14.6 |

EXPERIMENTAL

EXAMPLE 1

(2,4-Difluorophenyl)-pyridin-4-yl methanone (X)

219 ml (3.00 mole) of thionyl chloride were added to a solution of 246.2 g (2.00 mole) of isonicotinic acid in 500 ml of 1,2-dichloroethane and the mixture was refluxed for 4 hours. The excess thionyl chloride and the solvent were removed by evaporation at reduced pressure and 392 ml (4.00 mole) of 1,3-difluorobenzene and then, portionwise, 533 g (4.00 mole) of aluminium trichloride were added over the solid residue. Once the exothermal reaction has ended, the mixture was refluxed for 5 hours, it was cooled and poured over a mixture of 3 kg of ice and 1 kg of water, was stirred for 0.5 hours and the phases were separated. The aqueous phase was washed with 1L of methylene chloride, was than basified with 2L of 40% NaOH and extracted with Ch$_2$Cl$_2$ (2 x 1L). The combined organic extracts were dried (MgSO$_4$) and evaporated at reduced pressure to give 179.4 g (41% yield) of the title compound in the form of an ochre coloured oil.

IR (Film): 1680 cm$^{-1}$ $^1$H-NMR Δ(CDCl$_3$): 6.88–7.12 (m, 2H, arom.), 7.56–7.61 (m, 2H, pyrid.), 7.64–7.77 (m,1H,arom.), 8.81–8.85 (m,2H, pyrid.)

EXAMPLE 2

(2,4-Difluorophenyl)-pyridin-4-yl methanone oxime (VII)

62.6 g (0.900 mole) of hydroxylamine hydrochloride and 133.6 g (0.982 mole) of sodium acetate trihydrate were added to a suspension of 179.4 g (0.818 mole) of the compound of Example 1 in 1L of ethanol and the mixture was refluxed for 1 hour. The solvent was removed under low pressure evaporation, 1L of water was added to the residue and it was filtered. After drying for 3 hours at 45° C., 181 g (94% yield) of the title compound (mixture of sin- and anti-isomers) were obtained, as a white solid.

M.p.: 155°–200° C.

IR (KBr): 1580 cm$^{-1}$

1H-NMR δ(d6-DMSO):7.10–7.70 (m, 5H, arom. and pyrid.), 8.50–990 (m, 2H, pyrid.), 12.40 (sa, 1H, —OH)

EXAMPLE 3

6-Fluoro-3-pyridin-4-yl-benzo[d]isoxazole (V)

181 g (0.773 mole) of the oxime mixture of Example 2 were added portionwise to 19 g (0.4 mole) of a 50% suspension of NaH in mineral oil, suspended in 900 ml of tetrahydrofurane and stirred for 10 hours at 25°. The mixture was poured over 1L of water, the phases were separated and the aqueous phase was extracted with ethyl acetate (2 x 0.5L). The combined organic phases were dried (MgSO$_4$) and evaporated at reduced pressure. The residue was recrystallized from methanol twice, giving 53 g (32% yield) of the title compound as a white solid.

M.p.: 138°–146° C.

IR(KBr): 1610, 1595 cm$^{-1}$ $^1$H-NMR δ(CDCl$_3$): 7.15–7.27 (m, 1H, arom.), 7.35–7.45 (m, 1H, arom.), 7.80–7.95 (m, 3H, arom. and pyrid.) 8.80–8.88 (m, 2H, pyrid.)

EXAMPLE 4

1-[2-(2-methyl-4-oxo-6,7,8,9-tetrahydro-4H-pyrido[1,2-a] pyrimidin-3yl) ethyl]-4-(6-fluoro-benzo[d]isoxazol-3-yl)-pyridinium iodide (IV)

A suspension of 55 g (0.257 mole) of the compound of the previous Example, 64 g (0.282 mole) of 3-(2-chloroethyl)-2-methyl-6,7,8,9-tetrahydro-pyrido [1,2-a]pyrimidin-4-one (compound of formula VI, where W=Cl) and 42 g (0.282 mole) of sodium iodide 1L of acetonitrile was refluxed for 10 hours. After cooling to 10° C., it was filtered to give 135 g (98% yield) of the title compound as a yellow solid.

M.p.: 160°–166° C.

IR(KBr): 1630 cm$^{-1}$ $^1$H-NMR δ(DMSO): 165°–1.90 (m,4H, H-C(7) and H-C (8)), 2.15 (S,3H ,CH$_3$)

2.70–2.85 (m, 2H, H-C(9)), 3.05–3.25 (m,2H,CH$_2$-C(3)), 3.55–3.75 (m,2H,H-C(6)), 4.80–5.00 (m,2H,N$^+$-CH$_2$), 7.56 (dt, J=2.3,9.2,1H, arom.)

8.01 (dd, J=2.3, 8.5, 1H, arom.)

8.41 (dd, J=5.4, 9.2, 1H, arom.)

8.76 (d, J=6.9, 2H, pyrid)

9.28 (d, J=6.9, 2H, pyrid)

EXAMPLE 5

3-{2-[4-(6-fluoro-benzo[d]isoxazol -3-yl)-3,6-dihydro-2H-pyridin-1-yl]-ethyl }-2-methyl-6,7,8,9-tetrahydropyrido[1, 2-a]-pyrimidin-4-one (I)

6.0 g (0.158 mole) of NaBH$_4$ were added portionwise over a suspension of 50 g (0.094 mole) of the compound of the previous Example in methanol (0.5L), while holding the temperature to between 0° C. and 5° C. At the end of the addition, the mixture was stirred for a further 15 minutes, 50 g (0.935 mole) of $NH_4Cl$ were added and the methanol was removed by evaporation at reduced pressure. 150 ml of $H_2O$ and 30 ml of concentrated HCl were poured over the residue, it was heated until solution, 430 ml of IPA were added and the mixture was stirred for 5 hours at 20° C. After filtering, 21 g (53% yield) of the title compound were obtained, as dihydrochloride.

M.p.(base, DSC): 179° C.

IR (KBr): 1680 $cm^{-1}$ $^1$H-NMR δ($CDCl_3$): 1.80–2.10 (m, 4H, H-C(7) y H-C(8)), 2.35 (s,3H, $CH_3$), 2.55–2.75 (m, 1H, H-C(3)pyrid.), 2.75–2.95 (m, 9H, H-C(6), H-C(9), H-C(2)pyrid.

H-C(3)pyrid.,

C-$H_2$ C-$CH_2$-N 3.35–3.50 (m, 2H, H-C(6)pyrid.)

3.90–4.00 (m, 2H, N-$CH_2$-)

6.65 (sa, 1H, H-C(5)pyrid.)

7.05–7.15 (ddd, 1H, ar)

7.20–7.35 (dd, 1H, ar)

7.75–7.90 (dd, 1H, ar)

We claim:

1. 3-{2-[4-(6-Fluoro-benzo[d]isoxazol-3-yl)-3,6-dihydro-2H-pyridin-1-yl]-ethyl }-2-methyl-6,7,8,9-tetrahydropyrido [1,2-a]pyrimidin-4-one of formula (I)

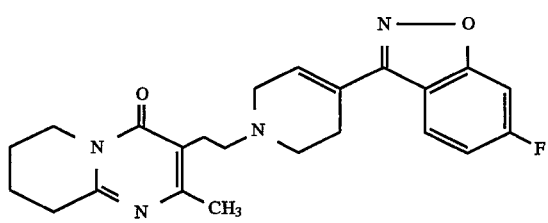

and the pharmaceutically acceptable salts thereof.

2. A process for the preparation of 3-{2-[4-(6-fluoro-benzo[d]isoxazol-3-yl)-3,6-dihydro-2H-pyridin-1-yl]-ethyl}-2-methyl-6,7,8,9-tetrahydropyrido [1,2-a]pyrimidin-4-one, comprising the partial reduction of a pyridinium salt of formula (IV):

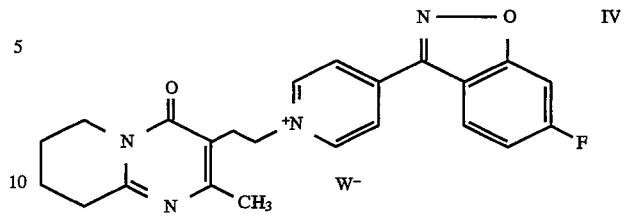

where $W^-$ is an organic or inorganic ion, by means of a metal borohydride in a protic solvent.

3. The process of claim 2, wherein the reduction is carried out with a metal borohydride.

4. The process of claim 3, wherein said metal borohydride is sodium borohydride.

5. The process of claim 2, wherein the reduction is conducted in a protic solvent medium.

6. The process of claim 5, wherein said solvent water, an alkanol or a carboxylic acid.

7. A process for the preparation of the compound of formula (IV), wherein a pyridine derivative of formula (V) is N-alkylated with an alkylizing reactant (VI):

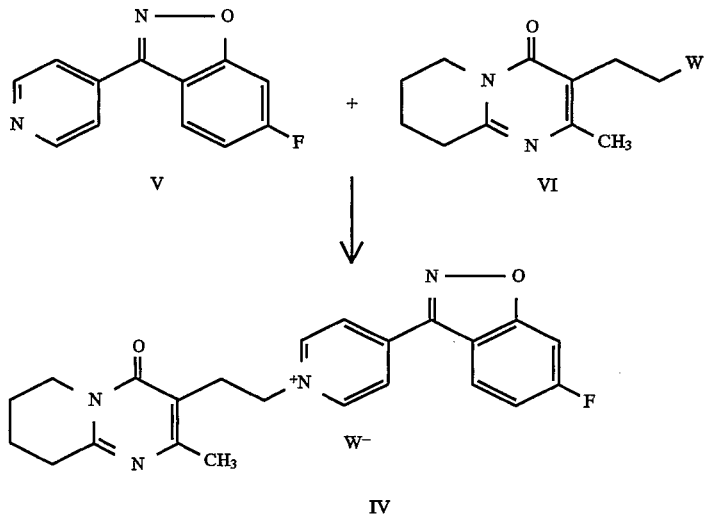

where $W^-$ is an organic or an inorganic ion, in an inert solvent.

8. A pharmaceutical composition containing 3-{2-[4-(6-fluoro-benzo[d]isoxazol-3-yl)-3,6-dihydro-2H-pyridin-1-yl]-ethyl}-2-methyl-6,7,8,9-tetrahydroprido [1,2-a] pyrimidin-4-one, or a pharmaceutically acceptable salt thereof, together with a pharmaceutically acceptable diluent.

9. The composition of claim 8, for human use, in the form of tablets, capsules, injectables or suspension.

10. A method of treating psychotic disorders which comprises administering to a patient in need of treatment an effective amount of 3-{2-[4-(6-fluoro-benzo[d]isoxazol-3-yl)-3,6 -dihydro-2H-pyridin-1-yl]-ethyl}-2-methyl-6,7,8,9-tetrahydropyrido [1,2-a]pyrimidin-4-one or a pharmaceutically acceptable salt thereof.

11. The process of claim 6, wherein said solvent is methanol.

12. The process of claim 7, wherein said process occurs at high temperature.

* * * * *